(12) United States Patent
Brown et al.

(10) Patent No.: US 10,167,238 B2
(45) Date of Patent: *Jan. 1, 2019

(54) MICRONUTRIENT COMPOSITIONS AND SYSTEMS AND METHODS OF USING SAME

(71) Applicant: Winfield Solutions, LLC, Shoreview, MN (US)

(72) Inventors: Danny Brown, Woodbury, MN (US); Jessica Drangeid, Bloomington, MN (US)

(73) Assignee: WINFIELD SOLUTIONS, LLC, Shoreview, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/874,447

(22) Filed: Jan. 18, 2018

(65) Prior Publication Data

US 2018/0141877 A1 May 24, 2018

Related U.S. Application Data

(63) Continuation of application No. 14/868,982, filed on Sep. 29, 2015, now Pat. No. 9,908,821.

(51) Int. Cl.
| | | |
|---|---|---|
| *A01N 43/70* | (2006.01) | |
| *A01N 57/20* | (2006.01) | |
| *A01N 25/06* | (2006.01) | |
| *A01N 37/36* | (2006.01) | |
| *A01N 37/44* | (2006.01) | |
| *A01N 59/16* | (2006.01) | |
| *C05D 9/02* | (2006.01) | |
| *C05G 3/00* | (2006.01) | |
| *C05G 3/02* | (2006.01) | |

(52) U.S. Cl.
CPC .............. *C05D 9/02* (2013.01); *A01N 25/06* (2013.01); *A01N 37/36* (2013.01); *A01N 37/44* (2013.01); *A01N 43/70* (2013.01); *A01N 57/20* (2013.01); *A01N 59/16* (2013.01); *C05G 3/0082* (2013.01); *C05G 3/02* (2013.01)

(58) Field of Classification Search
None
See application file for complete search history.

(56) References Cited

U.S. PATENT DOCUMENTS

| | | | |
|---|---|---|---|
| 2,960,406 A | 11/1960 | Cardon | |
| 3,493,557 A | 2/1970 | Ramsden | |
| 5,504,055 A * | 4/1996 | Hsu | A01N 59/06 504/121 |
| 5,997,600 A | 12/1999 | Frank | |
| 6,197,815 B1 | 3/2001 | Hsu | |
| 6,870,026 B1 | 3/2005 | Dean | |
| 7,666,242 B2 | 2/2010 | Gednalski et al. | |
| 8,685,133 B2 | 4/2014 | Ponder et al. | |
| 9,908,821 B2 * | 3/2018 | Brown | C05D 9/02 |
| 9,938,201 B1 * | 4/2018 | Scott | C05D 9/02 |
| 2005/0239673 A1 | 10/2005 | Hsu | |
| 2010/0273656 A1 * | 10/2010 | Sedun | A01N 37/32 504/319 |
| 2015/0250165 A1 | 9/2015 | Balastre | |

FOREIGN PATENT DOCUMENTS

WO WO 1993022919 11/1993

OTHER PUBLICATIONS

Bernards, Mark L. et al., "Glyphosate Interaction with Manganese in Tank Mixtures and Its Effect on Glyphosate Absorption and Translocation", Weed Science, vol. 53, No. 6 (Nov.-Dec. 2005), pp. 787-794.
Buhler, Douglas D. et al., "Effect of Water Quality, Carrier Volume, and Acid on Glyphosate Phytotoxicity", Weed Science, vol. 31, No. 2 (Mar. 1983), pp. 163-169.
Curran, W.S. et al., "Adjuvants for Enhancing Herbicide Performance", Penn State Extension, Agronomy Facts 37, pp. 1-5, downloaded from http://extension.psu.edu/pests/weeds/control/adjuvants-for-enhancing-herbicide-performance, May 2014.
Max-In® Zinc Label, Winfield, 3 pages, Nov. 2, 2015.
Max-In® Zinc Pamphlet, Winfield, 2 pages, 2015.
Max-In® Zinc Safety Data Sheet, Winfield, 5 pages, Mar. 20, 2015.
Mervosh, Todd L., et al. "Effects of Calcium, Magnesium, and Phosphate on Glyphosate Absorption by Cultured Plant Cells", Weed Science, vol. 39, No. 3 (Jul.-Sep. 1991), pp. 347-353.
Mueller, Thomas C. et al., "Comparison of Glyphosate Salts (Isopropylamine, Diammonium, and Potassium) and Calcium and Magnesium Concentrations on the Control of Various Weeds", Weed Technology, vol. 20, No. 1 (Jan.-Mar. 2006), pp. 164-171.
Roundup Weathermax MSDS, [online] (May 3, 2016), obtained from the URL <http://roundup.ca/_uploads/documents/Roundup%20WeatherMAX-Label_EN_04_16.pdf>.
Weed Control Alert, Guidelines for Use With AMS, Roundup PROMAX®, 2 pages, downloaded Feb. 2016, http://www.monsantoito.com/docs/PROMAX_Amonium_Sulfate_use_Hard_Water_issue_TUG.pdf.
Wyrill, J.B. III et al., "Glyphosate Toxicity to Common Milkweed and Hemp Dogbane as Influenced by Surfactants", Weed Science, vol. 25, No. 3 (May 1977), pp. 275-287.

* cited by examiner

*Primary Examiner* — Alton N Pryor
(74) *Attorney, Agent, or Firm* — Dorsey & Whitney LLP

(57) ABSTRACT

An agricultural spray may be produced by admixing citric acid and glutamic acid with a metal salt and a pesticide or other agricultural chemical containing components capable of precipitating with the metal salt in the admixture. The citric acid and the glutamic acid chelate with the metal salt to provide a stability and compatibility-enhancing composition, thereby preventing the metal salt from forming an insoluble solid within the admixture. Such a composition may be produced by admixing citric acid and glutamic acid at a molar ratio of about 6.8:0.5 to about 1:0.29. The composition may include a metal sat, citric acid and glutamic acid in a molar ratio of about 1:6.8:0.5 to about 1:1:0.29 and a pesticide.

20 Claims, 2 Drawing Sheets

MICRONUTRIENT COMPOSITIONS AND SYSTEMS AND METHODS OF USING SAME

CROSS-REFERENCE TO RELATED APPLICATION(S)

This application is a continuation of U.S. Ser. No. 14/868,982 filed Sep. 29, 2015, the contents of which are incorporated herein by reference.

TECHNICAL FIELD

The present disclosure relates to products, systems and methods for using compositions for improving the stability and compatibility of agricultural products, and more particularly, for improving the stability and the compatibility of micronutrients in agricultural mixtures.

BACKGROUND

Crop protection involves application of herbicides, insecticides, fungicides, collectively known as pesticides, to control the growth of weeds, harmful insects and plant diseases that afflict crops. Without these practices, food production would decline, many fruits and vegetables would be in short supply, and the price of food would rise. Further, fibers for textile manufacturing, such as cotton, would decrease as farmers would lose their harvests due to pests and diseases.

Pesticides are typically applied in combination with adjuvants to improve pesticide performance. Adjuvants are substances in a pesticide formulation or added to the spray tank to improve pesticidal activity or application characteristics. In addition, micronutrients may be applied in combination with pesticides and adjuvants. Micronutrients includes elements essential for plant growth and include boron (B), copper (Cu), iron (Fe), chloride (Cl), manganese (Mn), molybdenum (Mo) and zinc (Zn). For instance, boron assists plants in use and regulation of other nutrients, aids production of sugar and carbohydrates, and is required for seed and fruit development. Copper is important for reproductive growth, aids in root metabolism and helps in the utilization of proteins. Chloride aids plant metabolism. Iron is a necessary micronutrient in the formation of chlorophyll. Manganese is used by plant enzyme systems and is involved in the breakdown of carbohydrates, as well as nitrogen metabolism. Molybdenum assists in the use of nitrogen. Zinc is needed by the plant for regulating plant growth and in carbohydrate and sugar metabolism. While some micronutrients are found in soil, others are not; and some soil-based micronutrients may not be at levels sufficient for plant growth.

However, many pesticides contain phosphate salts that bind to the metal ions of the micronutrient and convert them to insoluble solids before the micronutrient can be absorbed by the plant, rendering micronutrient ineffective. In prior approaches, ethylenediaminetetraacetic acid (EDTA) has been used as a chelating compound that operates to bind metal ions of the micronutrient and prevents phosphate salt from converting the micronutrients to insoluble solids. While EDTA prevents phosphate from binding to metal ions, the metal ions exhibit diminished reactivity. In addition, EDTA is not accepted for use as a chelator in all countries. Other chelating compounds include organic acids and amino acids such as those described in U.S. Pat. No. 5,504,055 and US Patent Application Publication 2005/239673, which are incorporated herein for any purpose.

SUMMARY

Implementations provide compositions for use with agricultural chemicals containing components capable of precipitating with micronutrients (e.g., metal salts), and approaches for using these compositions.

According to certain implementations, a method of spraying an agricultural spray involves admixing a composition comprising citric acid and glutamic acid with a metal salt and a pesticide, the pesticide comprising phosphate, where the citric acid and the glutamic acid chelate with the metal salt to thereby prevent the metal salt from forming an insoluble solid with the phosphate.

In various implementations and alternatives, the citric acid and the glutamic acid are present in the composition at a molar ratio of about 6.8:0.5 to about 1:0.29; the metal salt is present with the citric acid and the glutamic acid at a molar ratio of about 1:6.8:0.5 to about 1:1:0.29; the metal salt is a metal salt of one or more of zinc, boron, copper, iron, chloride, manganese, molybdenum, cobalt, magnesium, calcium or nickel; the metal salt is a metal oxide; metal oxide is zinc oxide; the pesticide includes N-(phosphonomethyl) glycine and/or one or more of a salt, an ester or a derivative thereof.

According to another implementation, a method of producing a composition involves admixing a composition comprising citric acid and glutamic acid at a molar ratio of about 6.8:0.5 to about 1:0.29.

In various implementations and alternatives, the method further involves producing a chelated composition by mixing the composition with a metal salt, where the molar ratio of the chelated composition of the metal salt, the citric acid and the glutamic acid may be about 1:6.8:0.5 to about 1:1:0.29; producing an agricultural spray by mixing the chelated composition with a pesticide or a fertilizer. Such pesticides may include one or more of: N-(phosphonomethyl)glycine, 4-Dichlorophenoxyacetic acid, bentazon, 3,6-dichloro-o-anisic acid, 3,6-dichloro-2-methoxybenzoic acid, 1-chloro-3-ethylamino-5-isopropylamino-2,4,6-triazine, amide herbicides, arsenical herbicides, carbamate and tiocarbamate herbicides, carboxylic acid herbicides, dinitronailine herbicides, heterocyclic nitrogen-containing herbicides, organophosphate compounds, urea herbicides, quaternary herbicides, 5-[2-chloro-4-(trifluoromethyl)phenoxy]-N-(methylsulfonyl)-2-nitrobenzamide; tembotrione or derivatives thereof.

According to yet another implementation, an admixture of a composition includes a metal salt, citric acid and glutamic acid in a molar ratio of about 1:6.8:0.5 to about 1:1:0.29 and a pesticide.

In various implementations and alternatives, the metal salt is a metal salt of one or more of zinc, boron, copper, iron, chloride, manganese, molybdenum, cobalt, magnesium, calcium or nickel; the metal salt is a metal oxide such as zinc oxide; and the pesticide may include any of the aforementioned pesticides alone or in combination.

DETAILED DESCRIPTION

Figure 1A:
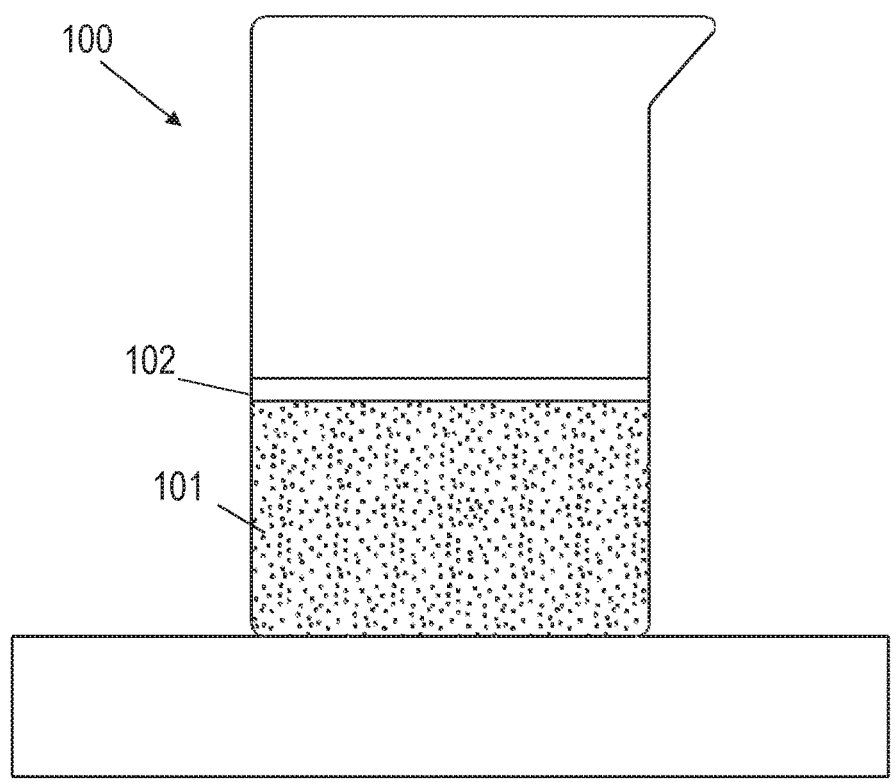
FIG. 1A is a photograph of a composition disclosed in the prior art.

Overview: Compositions of the present disclosure contain organic acids and amino acids at a ratio that binds (e.g., chelates) metal ions of the micronutrient to prevent salts (e.g. phosphate salts) commonly found in agricultural chemicals from converting the micronutrients to insoluble solids, while at the same time, prevents fouling of agricultural spray equipment or of pesticides. The compositions, accordingly, provide stability and compatibility for micronutrients in pesticides.

Metal ions commonly used in connection with the stability and compatibility-enhancing compositions include period 4 transition metals. These transition metals include, but are not limited to: V, Cr, Mn, Fe, Co, Ni, Cu, and Zn. Period 4 transition metals include six chelation sites. The disclosed compositions include coordination sites for chelating with such transition metals. For instance, citric acid has three coordination sites for chelation and glutamic acid has four chelation sites.

While prior approaches have used citric acid as a chelating agent that binds to metal ions, it has been discovered that the use of citric acid chelating agents results in problems when mixed with agricultural sprays (such as orthophosphate-based fertilizers including 9-18-9 fertilizers (i.e., 9% nitrogen-18% phosphate-9% potassium) and 7-23-5 fertilizers). For instance when used with glyphosate, e.g., Durango DMA, the citric acid is incompatible with the glyphosate and causes the precipitation of salts, which block screens and spray tips in agricultural spray applications. When used with, 2,4-Dichlorophenoxyacetic acid (2,4-D) and glyphosate, e.g., Enlist Duo, the citric acid results in breaking the emulsion. Further, some products that contain micronutrients that are not chelated are problematic when mixed with agricultural sprays. For instance, when micronutrients such as boron, zinc and manganese are mixed with glyphosate in its various forms (e.g., salts of glyphosate) as well as Basagran, amide herbicide nitro-phenol ethers including 5-[2-chloro-4-(trifluoromethyl)phenoxy]-N-(methylsulfonyl)-2-nitrobenzamide (e.g., Fomesafen), and orthophosphate-based fertilizers (e.g., 9-18-9 and 7-23-5 fertilizers), the combination results in precipitation of the metal ion. In another example, when micronutrients are combined with glyphosate in combination with other pesticides such as 2,4-Dichlorophenoxyacetic acid (2,4-D) (e.g., Enlist Duo), the result is a combination of precipitation of the metal ion and breaking the emulsion.

Description of the Embodiments: It has been discovered that the combination of citric acid in combination with glutamic acid at a molar ratio of about 1:0.29 to about 6.8:0.5 (where citric acid contains 192.1 g/mol, and glutamic acid contains 147.1 g/mol) provides a stability and compatibility-enhancing composition that is effective at preventing micronutrients from reacting with phosphate salts in agricultural compositions such as pesticides and fertilizers, while at the same time prevents fouling of agricultural spray equipment or of pesticides. In particular implementations, the composition may include a citric acid:glutamic acid molar ratio of about 14:1, 13:1, 12:1, 10:1, 9:1, 8:1, 7:1, 6:1, 5:1, 4:1, 3:1, 2:1, or 1:1. In some implementations, the preferred citric acid:glutamic acid molar ratios may be about 2:1 or 0.9:0.5.

The disclosed compositions may be used in, or may include, a variety of micronutrients in the form of metal ions including water soluble salts of zinc, boron, copper, iron, chloride, manganese, molybdenum, cobalt, magnesium, calcium, and nickel or mixtures thereof. For instance, the metal salts may include the water soluble salts, sulfates, nitrates, hydroxides, acetates, carbonates, chlorides, phosphates or mixtures thereof. In some implementations, the preferred metal salts includes zinc salts such as zinc sulfate ($ZnSO_4$), zinc nitrate ($Zn(NO_3)_2$), zinc oxide (ZnO), zinc chloride ($ZnCl_2$), zinc chlorate $Zn(ClO_3)_2$, zinc phosphate ($Zn_3(PO_4)_2$), zinc molybdate ($ZnMoO_4$), zinc chromate ($ZnCrO_4$), zinc fluoride ($ZnF_2$), zinc bromide ($ZnBr_2$) and zinc cyanide ($Zn(CN)_2$). Other preferred metal salts may include metal sulfates such as zinc sulfate ($ZnSO_4$).

More particularly, the disclosed compositions may be chelated compositions that provide a stable micronutrient formula that is also compatible with soil and foliar nutrients and/or pesticide mixes. In some implementations, the chelated compositions may include a metal oxide, citric acid and glutamic acid at a molar ratio ranging from about 1:6.8:0.5 to about 1:1:0.29. In particular implementations, the chelated compositions may include a metal salt:citric acid:glutamic acid molar ratio of about 2:14:1, 2:13:1, 2:12:1, 2:10:1, 2:9:1, 2:8:1, 2:7:1, 2:6:1, 2:5:1, 2:4:1, 2:3:1, 2:2:1, 1:0.9:0.5, or 1:1:0.29. A zinc oxide:citric acid:glutamic acid molar ratio of, 2:2:1, 1:0.9:0.5, or 1:1:0.29 may be preferred in some implementations (e.g., with 81.4 g/mol ZnO: 192.1 g/mol citric acid: 147.1 g/mol glutamic acid).

According to some implementations, the compositions of the present disclosure may be free of other chelating agents such as ethylenediaminetetraacetic acid (EDTA) and variations thereof such as its conjugate base ethylenediamine tetraacetate (e.g., tetrasodium ethylenediamine tetraacetate). Particularly, the combination of citric acid and glutamic acid is effective to bind the metal ions of the micronutrient and prevents phosphate salt from converting the micronutrients to insoluble solids without requiring the use of other commonly known chelating agents such as EDTA. The application of the organic acids of the present disclosure without EDTA can additionally be useful in avoiding phytotoxicity, e.g., burning. In addition or alternatively, the chelating agents in the disclosed compositions may consist of or consist essentially of glutamic acid and citric acid. Such chelating agents may be chelated with one or more metal ions and/or may be present in the admixture in excess. Other components such as water, defoaming agents, a source of sugar, surfactants, biocides, propylene glycol, sodium hydroxide, may be present in the disclosed compositions, for instance, as necessary components for the manufacture and distribution of the stability and compatibility-enhancing product, without affecting the effectiveness of the chelating components.

A number of pesticides, e.g., herbicides, insecticides and/or fungicides are compatible with the compositions of the present disclosure. These herbicides include but are not limited to: N-(phosphonomethyl)glycine, e.g., glyphosate, in various forms including in the form of a salt, ester or other derivative thereof. Examples of glyphosate products include but are not limited to: its form as a potassium salt (e.g., Roundup PowerMax and Touchdown Total), as a dimethylamine salt (e.g., Durango DMA), in is form as an isopropylamine salt (e.g., Cornerstone 5+), and glyphosate in combination with other pesticides such as 2,4-Dichlorophenoxyacetic acid (2,4-D) (e.g., Enlist Duo) and with dicamba (e.g., Mon 76832 and Roundup Xtend).

Other compatible herbicides include, but are not limited to: the sodium salt of bentazon (3-(1-methylethyl)-1H-2, 1,3-benzothiadiazin-4 (3H)-one 2,2,-dioxide) (e.g., Basagran); diglycolamine salt of 3,6-dichloro-o-anisic acid (e.g., Sterling Blue); 3,6-dichloro-2-methoxybenzoic acid (e.g., Dicamba, Enginia); 2,4-Dichlorophenoxyacetic acid (2,4-

D); 1-chloro-3-ethylamino-5-isopropylamino-2,4,6-triazine (Atrazine); amide herbicides; arsenical herbicides; carbamate and tiocarbamate herbicides; carboxylic acid herbicides; dinitronailine herbicides; heterocyclic nitrogen-containing herbicides; organophosphate compounds; urea herbicides; and quaternary herbicides; 5-[2-chloro-4-(trifluoromethyl) phenoxy]-N-(methylsulfonyl)-2-nitrobenzamide (Fomesafen); tembotrione (e.g., Laudis).

Weeds that may be controlled using the herbicide compositions may include, but are not limited to: barnyard grass, green foxtail, wild oats, nightshade, velvetleaf, annual morningglory, yellow nutsedge, pigweed, downy brome.

According to certain implementations, compatible herbicides may include nitrogen, phosphorus and potassium elements, in a ratio that allows the composition to function as both a herbicide and a fertilizer. Fertilizers that may be compatible with the compositions of the present disclosure may include but are not limited to N-P-K fertilizers such as 9-18-9 and 10-34-0 fertilizers and atrazine-containing fertilizers.

In addition or alternatively, the herbicides may include insecticides and/or fungicides. Insecticides that may be compatible with the disclosed compositions include but are not limited to: pyrethroid insecticides (e.g., bifenthrin); pyrethrins or other botanicals (e.g. D-limonene, linalool, ryania, rotenone, eugenol (clove oil); chloronicotinyls; essential oils (e.g., lemongrass, pepper wintergreen, rosemary, cinnamon, sesame, thyme, cedar oils and capsaicin); neem oil (e.g., Azadirachtin); nicotine; microbial products (e.g., *Bacillus thuringeinis* and *Beauveria bassiana*); oxadiazines (e.g., Indoxacarb); anthranilic diamide (e.g., chlorantraniliprole); juvenile hormone mimics (e.g., fenoxycarb; pyriproxifen; methoprene; and hydroprene), pyrroles (e.g., chlorfenapyr), phenylpyrazoles (e.g., fipronil), organophosphates (e.g., malathion and chlorpyrifos), inorganics (e.g., sulfur and dormant and horticultural oils); insect growth regulators such as chitin synthesis inhibitors (e.g., hexaflumuron; noviflumuron; diflubenzuron; buprofezine; cyromazine; and halofenozide); acaricides such as miticides (e.g., avermectin) and ixodicides alone or in any combination with the compositions of the present disclosure. Fungicides that may be compatible with the disclosed compositions include but are not limited to: fluxapyroxad, pyraclostrobin, propiconazole, trifloxystrobin, prothioconazole, 1,2-propanediol, azoxystrobin (e.g. Priaxor, On Set, Topaz, Headline amp, Headline sc, Stratego, Quadris) alone or in any combination with the compositions of the present disclosure.

In addition, fertilizers alone (e.g., not necessarily in the presence of a pesticide) may be compatible with the compositions of the present disclosure and may include but are not limited to N-P-K fertilizers such as 9-18-9 and 10-34-0 fertilizers.

Figure 1B:
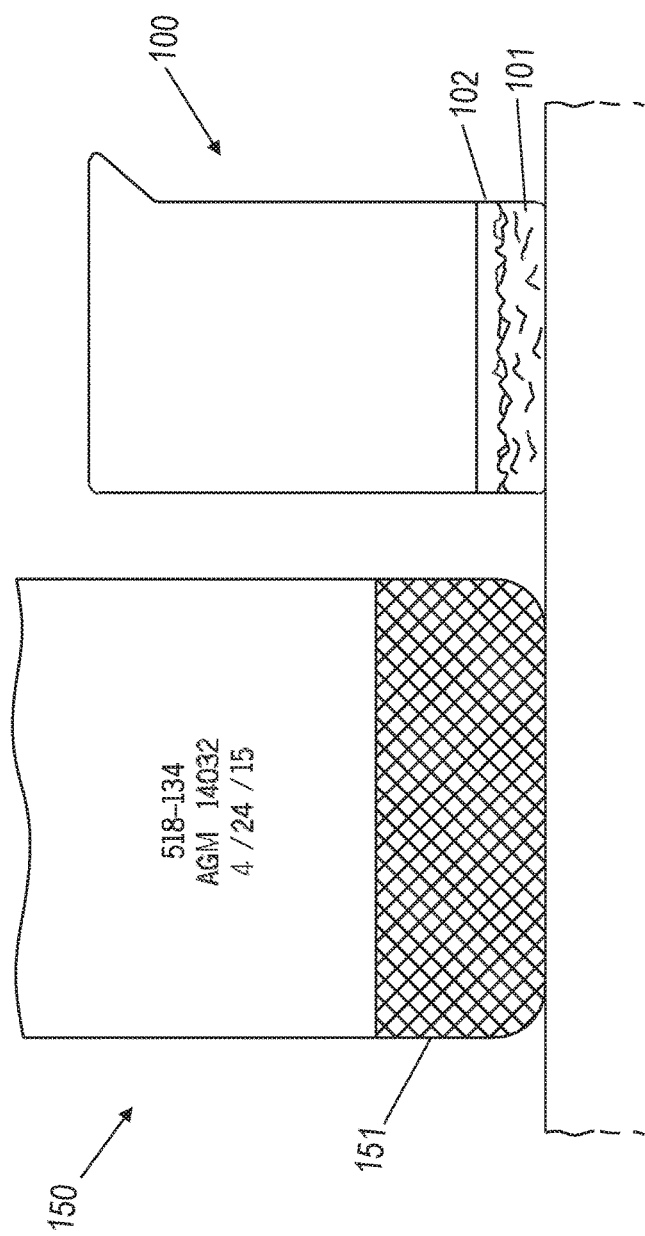
FIG. 1B (left) is a photograph of a chelated composition of the present disclosure and (right) of the composition disclosed in the prior art.

The compositions of the present disclosure differ from an approach disclosed in U.S. Pat. No. 5,504,055 (the '055 patent) in which a zinc oxide/citrate/glutamate chelate was prepared by deaerating water and combining zinc oxide, citric acid and glutamic acid at a ratio of 3:1:10 by weight (i.e., a molar ratio of 1:0.16:2, with 81.4 g. zinc oxide, 30 g. citric acid, 294.2 g. glutamic acid) to form an aqueous solution that was subsequently dried to form a zinc amino acid chelate. While the chelate of the '055 patent was described as improving plant performance when combined with plant nutrients over a control that does not use such a zinc amino acid chelate, studies of this chelate show that it is not stable and therefore cannot be applied in agricultural settings. Particularly, FIGS. 1A and 1B (right side) are illustrations of pictures showing a zinc oxide/citrate/glutamate mixture (100) at a molar ratio of 1:0.16:2 that was prepared according to the method described in Example XI of the '055 patent; while the left side of FIG. 1B, i.e., the container labeled AGM 14032 (150), is an illustration of an image of the composition of the present disclosure at a 2:2:1 ratio of zinc oxide:citric acid:glutamic acid. The picture represented in the illustration of FIG. 1A was taken 24 hours after stirring the '055 patent mixture and prior to filtration. The opaque layer (101) is the zinc ion converted to an insoluble, white solid, and the clear layer (102) is citric acid in water. Prolonged stirring was an attempt to cause the components to dissolve in solution. The picture of the '055 patent mixture represented in the illustration in FIG. 1B (100) was taken 24 hours after filtration and shows an opaque mixture of precipitated solids (101) below a clear layer (102). Consequently, the zinc oxide/citrate/glutamate molar ratio of 1:0.16:2 does not form a stable composition. In contrast, the left side of FIG. 1B shows an illustration of a picture of the AGM 14032 mixture (150) taken 24 hours after mixing where the citrate and glutamate has chelated with the zinc ions, which results in the mixture being clear orange (151) (represented as diamond cross-hatch) due to the non-precipitation of the zinc in the mixture. The mixture remained in this stable, non-precipitated state for over 42 days.

Production of the Stability and Compatibility-Enhancing Composition

To produce the chelated compositions of the present disclosure, a metal oxide (e.g., zinc oxide), glutamic acid, citric acid, and an amount of sodium hydroxide needed to raise the pH to 7.5 may be mixed with water and agitated at about 130° F. until all raw materials are solubilized and the mixture is clear and colorless. Water may be added to achieve the desired volume and the mixture agitated until the product is homogenous. The metal oxide, glutamic acid, and citric acid may be added in any order. In one implementation, the mixture may contain 7.5% zinc oxide, 18.4% citric acid, and 7.1% glutamic acid (e.g., at a molar ratio of 2:2:1). The mixture of components yields an exothermic reaction and the temperature of the mixture was monitored and maintained at a temperature below 165° F., preferably below 165° F. During production, the pH of the mixture is acidic (e.g., at a pH of about 3) and may be adjusted to about 7.5. The final pH of the product after 24 hours is about 8.0.

The chelated compositions may be converted to a solid such as water-soluble powders, granules and/or prills. In addition or alternatively, the compositions may be combined with micronutrients and the chelate may be converted to a solid.

The chelated compositions of the present disclosure are stable under various conditions, including but not limited to: freeze/thaw conditions ($-18°$ C.$\pm 2°$ C.) for over five cycles, refrigerator conditions ($0°$ C.$\pm 2°$ C.) for over three months, elevated temperatures ($54°$ C.$\pm 2°$ C.) for over five weeks, which equates to a shelf-life at room temperature of more than 12 months. Particularly, per ASTM protocols, a mixture that is stable under oven conditions at $54°$ C. for two weeks is equivalent to a 12-month shelf-life at room temperature, meaning the compositions of the present disclosure that are stable for five weeks have a shelf life that exceeds 12 months.

In addition, the chelated compositions of the present disclosure are compatible with the disclosed pesticides including but not limited to: glyphosate, 2,4-D, Sterling Blue, Basagran, Atrazine, Enginia, Enlist duo and derivatives thereof. Particularly, mixtures of the disclosed compositions and the pesticides do not exhibit flocculation, sludge, gelling, clumping, precipitation, separation, or non-dispersible oil over common test periods such as 15 minutes, 2 hours, 6 hours or 24 hours or extended periods of time, such as 72 hours, or at least one, two, three, four, five or six weeks.

Methods of Use:

The disclosed compositions may be applied in agricultural spray applications such as to seed, soil, foliage and fruit. Such sprays may be delivered using ground and aerial applications.

Prior to use, the disclosed compositions may be mixed with, for instance, water, micronutrients, pesticides, antimicrobial compositions, defoamers, adjuvants (e.g., alkyl polyglycosides), monosaccharaides (e.g., high fructose corn syrup), disaccharides, formulation aids (e.g., propylene glycol), surfactants (e.g., cationic, anionic and/or nonionic) and pH adjusters. Mixing may be conducted under agitation and may take place at ambient temperatures, e.g., about 70 to 90° F. depending on climate, or may take place under elevated temperatures above 90° F. The stability and compatibility-enhancing compositions (e.g., chelated compositions) may have a pH of about 8.0 prior to mixing.

The compositions of the present disclosure perform similarly or better than chelated products containing EDTA with respect to micronutrient uptake by the plant without causing phytotoxicity. The compositions additionally provide benefits over the use of EDTA due to environmental fate questions in connection with its use.

EXAMPLES

Stability

A stability and compatibility-enhancing composition of zinc oxide, citric acid and glutamic acid at a molar ratio of 2:2:1 was subjected to stability testing using a procedure modified from CIPAC MT 39 and CIPAC MT 46.3, and involved freeze/thaw, refrigerator, and oven stability testing.

Materials and Methods:

The apparatuses used in the stability testing included: a graduated jar, 120 mL; a flashlight; an oven, controlled to a specified temperature (±2° C.); and a refrigerator/freezer controlled to a specified temperature (±2° C.).

The freeze/thaw stability testing procedure involved transferring an amount of product into a graduated jar; placing the jar into the freezer at −18° C.±2° C.; after 24 hours, the sample was taken out of the freezer and allowed to come to room temperature; upon reaching room temperature, the product had undergone one cycle. The sample was subjected to five (5) total cycles.

Freeze/thaw evaluation was conducted after each cycle and observations were taken for any disruption in product formulation including but not limited to, phasing, creaming, settling, crystal growth, precipitation, changes in color, and/or discoloration of container. A flashlight was used to observe darker formulations. If changes in formulation were noticed, numbers of inversions required to get product homogenous was be recorded. If inversion of the product did not homogenize product, the test was considered a fail.

Using refrigeration to test stability involved transferring product into a graduated jar; placing the jar into a refrigerator at 0° C.±2° C.; and checking for any change every day for four weeks. After the four week period, the product was checked once a week. The product was tested for three months.

Stability evaluation for refrigeration was conducted each time the product was checked, and observations were taken and recorded according the method described in connection with the freeze/thaw evaluation.

Testing stability under elevated temperatures involved using an oven. An amount of product was transferred into a graduated jar and placed into an oven at 54° C.±2° C. The product was checked for any change every day for four weeks. After four weeks, the product was checked once a week. The product was allowed to stay in the oven for 3 months.

Stability evaluation under elevated temperature was conducted each time the product was checked, and observations were taken and recorded according the method described in connection with the freeze/thaw evaluation.

Results:

The results of the stability testing showed the composition was stable under freeze/thaw conditions for over five cycles; was stable in refrigerator conditions for over three months; and was stable under heat for over five weeks, which equates to a shelf-life of more than 12 months.

Compatibility

The stability and compatibility-enhancing composition containing zinc oxide, citric acid and glutamic acid at a molar ratio of 2:2:1 was tested for compatibility with pesticides using a modified approach from ASTM E1518-05(2012), Standard Practice for Evaluation of Physical Compatibility of Pesticides in Aqueous Tank Mixtures by the Dynamic Shaker Method, ASTM International, West Conshohocken, Pa., 2012. The pesticides tested included: glyphosate including in its various forms including Roundup Power Max, Durango, Cornerstone 5+, Touchdown Total; 2,4-D; Sterling Blue; Basagran; Atrazine; Enginia; Enlist duo and Roundup Xtend.

Materials and Methods:

The apparatuses used in compatibility testing included: 1. a graduated cylinder, 120 mL; 2. transfer pipets; 3. balance, ±0.01 g; 4. a sieve, U.S. standard, 50 mesh (300 μm), 3 inches in diameter; and 5. a flashlight. With respect to the reagents used, reagent grade chemicals were used in all tests and the water had a purity level of Type IV. Synthetic water was made according to CIPAC handbook F section MT18.

The final disposition of the compatibility test was on or around 100 mL, and the ratios needed to bring an application of 10 gallons per acre to 100 mL per acre were calculated. 70 percent of the water needed for the compatibility test was added to the cylinder at room temperature. The remaining components were added for the jar test according to WALES and DALES unless otherwise specified by the product label. Applications rates were used from the product label. The liquid products were delivered using the transfer pipet or weigh in solid products. After each individual product had been added, the jar was capped and swirled by hand until the product became homogenous. After all of the product water had been added, the remaining the water was be added. The entire mix was agitated for a period of no less than 30 seconds.

Testing and evaluations were conducted 0.25, 2, 6, 24, and 72 hours after agitating the mixture. Evaluations were separated into seven categories that are flocculation, sludge, gelling, clumping, precipitation, separation, and non-dispersible oil. A grading of 1-5 was used for each category (1 being the presence of none, 5 having the highest presence).

Results:

The results of the compatibility testing showed the composition did not have any flocculation, sludge, gelling, clumping, precipitation, separation, or non-dispersible oil after 42 days. All categories for each of the herbicides tested scored a 1 over this time period.

Uptake/Efficiency

This zinc foliar uptake trial was conducted at River Falls, Wis. and Rosemount, Minn. during the 2015 corn growing season. The trial was laid out on a randomized-complete block design with four replications. Plot size was 10 feet by 30 feet. An equivalent amount of zinc, 0.11 lb./acre, was applied foliarly to corn at a 10 gallon/acre total application rate to each plot utilizing four different products with analysis in parenthesis: a stability and compatibility-enhancing composition of the present disclosure (0-0-0-6.0Zn) containing ZnO/citric acid/glutamic acid at molar ratio of 1:1:0.5; Ultra-Che Zinc 9% EDTA (7-0-0-9Zn) (derived from zinc diammonium ethylenediaminetetracetate (EDTA)); and Citri-Che Zinc 10% (6-0-0-10Zn) (derived from: zinc chloride, zinc oxide, zinc EDTA, citric acid and ammonium hydroxide). All products tested were chelated. The composition of the present disclosure was free of EDTA and its derivatives, while the two compositions tested contained chelated EDTA.

Prior to the foliar application of the zinc-containing products, a composite tissue sample, comprised of the uppermost, fully developed corn leaf, was collected from across the trial area. This sample established the pre-existing zinc content of the corn plants.

Zinc uptake from a foliar application of the disclosed composition applied to corn at the V4 growth stage was measured by plant tissue analysis. A plant tissue sample was collected from each plot six days post-application. The sample was the uppermost, fully developed corn leaf taken from every plant from the center two rows of the plot. The center two rows were the only rows utilized to ensure the plants sampled received even coverage during product application and to eliminate the potential for spray-overlap. The corn tissue was analyzed by Midwest Laboratories (13611 B Street, Omaha, Nebr. 68144).

Results:

The results of Table 1 illustrate that the disclosed composition of the present disclosure performs similarly or better than the chelated products containing EDTA.

TABLE 1

| Product | % Zinc | Rate | Average Corn Tissue Zinc (ppm) | % Zinc Increase |
|---|---|---|---|---|
| Untreated Check | — | — | 31 | — |
| Glutamic acid/citric acid chelated with zinc (from ZnO) | 6% | 20.7 fl. oz./acre | 34.25 | 10.5% |
| Ultra-Che Zinc 9% (with EDTA) | 9% | 14 fl. oz./acre | 32.75 | 6.5% |
| Citri-Che Zinc 10% (with EDTA) | 10% | 13.5 fl. oz./acre | 35 | 12.9% |

While methods disclosed herein have been described and shown with reference to particular operations performed in a particular order, it will be understood that these operations may be combined, sub-divided, or re-ordered to form equivalent methods without departing from the teachings of the present disclosure. Accordingly, unless specifically indicated herein, the order and grouping of the operations should not be construed as limiting.

Similarly, it should be appreciated that in the foregoing description of example embodiments, various features are sometimes grouped together in a single embodiment or description thereof for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

While the present disclosure has been particularly shown and described with reference to embodiments thereof, it will be understood by those skilled in the art that various other changes in the form and details may be made without departing from the spirit and scope of the disclosure.

What is claimed is:

1. A method of spraying an agricultural spray admixture, comprising:
   spraying an admixture comprising citric acid and glutamic acid with a metal salt and a pesticide, the pesticide comprising phosphate, the metal salt comprising one or more zinc, boron, copper, iron, chloride, manganese, molybdenum, cobalt, magnesium, calcium, or nickel;
   wherein the citric acid glutamic acid and metal salt form a chelate to thereby prevent the metal salt from forming an insoluble solid with the phosphate, and
   wherein the citric acid and the glutamic acid are present in the composition at a molar ratio of about 6.8:0.5 to about 1:0.29,
   wherein the admixture remains stable, non-precipitated for at least 72 hours.

2. The method of claim 1, wherein the metal salt is present with the citric acid and the glutamic acid at a molar ratio of about 1:6.8:0.5 to about 1:1:0.29.

3. The method of claim 1, wherein the pesticide comprises N-(phosphonomethyl)glycine.

4. The method of claim 1, wherein the composition further includes at least one insecticide and/or at least one fungicide.

5. The method of claim 1, wherein the composition is free of ethylenediaminetetraacetic acid.

6. The method of claim 1, wherein the composition does not exhibit at least one of flocculation, sludge, gelling, clumping, precipitation, separation, or non-dispersible oil over at least one week.

7. The method of claim 1, wherein the admixture remains stable, non-precipitated for at least 42 days.

8. A method of producing a stability and compatibility-enhancing composition, comprising:
   admixing a composition comprising citric acid and glutamic acid at a molar ratio of about 6.8:0.5 to about 1:0.29, the composition further comprising a metal salt, the metal salt comprising one or more of zinc, boron, copper, iron, chloride, manganese, molybdenum, cobalt, magnesium, calcium, or nickel; wherein the citric acid, glutamic acid and metal salt form a chelate; and
   wherein the composition remains stable, non-precipitated over 72 hours.

9. The method of claim 8, wherein the molar ratio of the chelated composition of the metal salt, the citric acid and the glutamic acid is about 1:6.8:0.5 to about 1:1:0.29.

10. The method of claim 8, wherein the metal salt includes a metal oxide.

11. The method of claim 8, wherein the composition does not exhibit at least one of flocculation, sludge, gelling, clumping, precipitation, separation, or non-dispersible oil over at least one week.

12. The method of claim 8, wherein the composition remains stable, non-precipitated for at least 42 days.

13. The method of claim 8, further comprising producing an agricultural spray by mixing the composition with one or more of a pesticide or a fertilizer.

14. The method of claim 13, wherein the composition comprises at least the pesticide, the pesticide comprising one or more of: N-(phosphonomethyl)glycine, 4-Dichlorophenoxyacetic acid, bentazon, 3,6-dichloro-o-anisic acid, 3,6-dichloro-2-methoxybenzoic acid, 1-chloro-3-ethylamino-5-isopropylamino-2,4,6-triazine, amide herbicides, arsenical herbicides, carbamate and tiocarbamate herbicides, carboxylic acid herbicides, dinitronailine herbicides, heterocyclic nitrogen-containing herbicides, organophosphate compounds, urea herbicides, and quaternary herbicides, 5-[2-chloro-4-(trifluoromethyl)phenoxy]-N-(methylsulfonyl)-2-nitrobenzamide, tembotrione or an ester of the pesticide.

15. The method of claim 8, wherein the composition is a solid.

16. A stability and compatibility-enhancing admixture of a composition comprising a metal salt, citric acid and glutamic acid in a molar ratio of about 1:6.8:0.5 to about 1:1:0.29 and a pesticide, the metal salt comprising one or more of zinc, boron, copper, iron, chloride, manganese, molybdenum, cobalt, magnesium, calcium, or nickel; wherein the citric acid, glutamic acid and metal salt form a chelate; and
wherein the admixture remains stable, non-precipitated for at least 72 hours.

17. The admixture of claim 16, wherein the pesticide comprises one or more of: N-(phosphonomethyl)glycine, 4-Dichlorophenoxyacetic acid, bentazon, 3,6-dichloro-o-anisic acid, 3,6-dichloro-2-methoxybenzoic acid, 1-chloro-3-ethylamino-5-isopropylamino-2,4,6-triazine, amide herbicides, arsenical herbicides, carbamate and tiocarbamate herbicides, carboxylic acid herbicides, dinitronailine herbicides, heterocyclic nitrogen-containing herbicides, organophosphate compounds, urea herbicides, and quaternary herbicides, 5-[2-chloro-4-(trifluoromethyl)phenoxy]-N-(methylsulfonyl)-2-nitrobenzamide, tembotrione or an ester of the pesticide.

18. The admixture of claim 16, wherein the composition does not exhibit at least one of flocculation, sludge, gelling, clumping, precipitation, separation, or non-dispersible oil over at least one week.

19. The admixture of claim 16, wherein the admixture remains stable, non-precipitated for at least 42 days.

20. The admixture of claim 16, wherein the composition is free of ethylenediaminetetraacetic acid.

* * * * *